(12) United States Patent
Kachlany et al.

(10) Patent No.: US 9,724,384 B2
(45) Date of Patent: Aug. 8, 2017

(54) METHODS TO TREAT INFLAMMATION OF THE LUNG

(71) Applicants: RUTGERS, THE STATE UNIVERSITY OF NEW JERSEY, New Brunswick, NJ (US); Benjamin Belinka, Kendall Park, NJ (US)

(72) Inventors: Scott Kachlany, Bridgewater, NJ (US); Benjamin Belinka, Kendall Park, NJ (US)

(73) Assignees: Rutgers, the State University of New Jersey, New Brunswick, NJ (US); Actinobac Biomed, Inc., Kendall Park, NJ (US)

( * ) Notice: Subject to any disclaimer, the term of this patent is extended or adjusted under 35 U.S.C. 154(b) by 0 days.

(21) Appl. No.: 14/745,297

(22) Filed: Jun. 19, 2015

(65) Prior Publication Data

US 2015/0366937 A1    Dec. 24, 2015

Related U.S. Application Data

(60) Provisional application No. 62/014,967, filed on Jun. 20, 2014.

(51) Int. Cl.
| | | |
|---|---|---|
| *A61K 39/02* | (2006.01) | |
| *A61K 45/00* | (2006.01) | |
| *A61K 39/00* | (2006.01) | |
| *A61K 38/16* | (2006.01) | |
| *A61K 9/00* | (2006.01) | |
| *C07K 14/195* | (2006.01) | |

(52) U.S. Cl.
CPC ............ *A61K 38/164* (2013.01); *A61K 9/008* (2013.01); *A61K 9/0075* (2013.01); *A61K 9/0078* (2013.01); *A61K 39/02* (2013.01); *C07K 14/195* (2013.01)

(58) Field of Classification Search
CPC ........ A61K 39/00; A61K 39/02; A61K 39/04; A61K 38/19
USPC .......... 424/184.1, 185.1, 234.1, 236.1, 278.1
See application file for complete search history.

(56) References Cited

U.S. PATENT DOCUMENTS

| | | | |
|---|---|---|---|
| 9,352,017 B2 | 5/2016 | Kachlany et al. | |
| 2009/0075883 A1 | 3/2009 | Kachlany | |
| 2009/0257957 A1 | 10/2009 | Burnier et al. | |
| 2012/0263644 A1* | 10/2012 | Kachlany | ............ A61K 38/164 424/1.49 |

FOREIGN PATENT DOCUMENTS

| | | |
|---|---|---|
| WO | 2007062150 A2 | 5/2007 |
| WO | 2011047011 A2 | 4/2011 |

OTHER PUBLICATIONS

International Search Report and Written Opinion issued Sep. 29, 2015, in Application No. PCT/US2015/036814.
Walker et al.: "Toward an AIDS Vaccine", Science, 2008, No. 320, pp. 760-764.
Pantaleo, et al.: "Correlates of Immune Protection in HIV-1 Infection: What We Know, What We Don't Know, What We Shoud Know", Nature Medicine, Aug. 2004, vol. 10, No. 8, pp. 806-810.
Global Campaign for Microbicides: "Understanding HIV Drug Resistance", 2009, pp. 1-2.
DiFranco, et al: "LFA-1-Targeting Leukotoxin (LtxA; Leukothera®) Causes Lymphoma Tumor Regression in a Humanized Mouse Model and Requires Caspase-8 and Fas to Kill Malignant Lymphocytes", Leuk Res. Jun. 2015, 39 (6), pp. 649-656.

* cited by examiner

*Primary Examiner* — Rodney P Swartz
(74) *Attorney, Agent, or Firm* — Fox Rothschild LLP

(57) ABSTRACT

The present invention provides pharmaceutical compositions comprising leukotoxin for the treatment of lung inflammation.

15 Claims, 3 Drawing Sheets

METHODS TO TREAT INFLAMMATION OF THE LUNG

CROSS-REFERENCE TO RELATED APPLICATION

This application claims priority of U.S. Provisional Application No. 62/014,967 filed on Jun. 20, 2014. The content of the application is incorporated herein by reference in its entirety.

GOVERNMENT INTERESTS

The invention disclosed herein was made, at least in part, with government support under Grant No. R21CA167238 from the National Institutes of Health. Accordingly, the U.S. Government has certain rights in this invention.

FIELD OF THE INVENTION

The invention relates to pharmaceutical compositions, and methods for treating lung inflammation.

BACKGROUND OF THE INVENTION

Lung inflammation is characterized by the massive infiltration of activated white blood cells (WBCs) in the lung and airway subsequent to many immune related causes. Although some treatments are available to treat the underlying disease, many of these diseases do not have a cure and are chronic diseases, or the treatment for the disease is not immediately effective, and the resulting lung inflammation remains a health concern for the patient. Steroids are used as an adjunct therapy to treat lung inflammation, however the chronic use of steroids often leads to multiple side effects such as proximal myopathy, cushingoid habitus, hyperglycemia, diabetes, infections and osteoporosis. Other drugs are known to down regulate the immune system, but many of these drugs are unable to differentiate between resting and activated immune cells, and generally have a potent immunosuppression effect. Thus, there is a need for new treatments to reduce lung inflammation caused by many diseases and immune related disorders, with minimal immunosuppression and associated side effects.

In lung related disorders, various subtypes of WBCs show up-regulation and activation of Lymphocyte function-associated antigen 1 ("LFA-1"). The activated LFA-1 then mediates the migration of WBCs into the airways. Once migrated, the inflammatory WBCs cause airway inflammation and bronchial remodeling that can lead to adverse effects in a subject if the inflammation is uncontrolled.

Lung inflammation is a general term for inflammation affecting any part of the lung or surrounding tissue and fluid, and the up-regulation of certain cytokines. Clinical characteristics of lung inflammation may include shortness of breath, increased fluid and/or mucus in the lungs, increased coughing, associated pain when breathing and inability to breathe. The treatment for lung inflammation is aimed at reducing inflammation and the associated clinical symptoms caused by uncontrolled lung inflammation.

Agents that target LFA-1 have been used to treat asthma, a chronic disorder that causes lung inflammation, including, for example, simvastatin, a small molecule drug that can target LFA-1, and efalizumab, a monoclonal antibody against LFA-1. In randomized controlled trials of asthma patients, simvastatin was shown to reduce airway and sputum eosinophilia, but it did not affect airway hyperresponsiveness or reduce the expression of inflammatory cytokines (IL-4, 5) compared to the placebo. Treatment of asthma patients with efalizumab, by blocking LFA-1 caused while the drug is bound to the receptor, caused a decrease in the number of inflammatory cells as well as a decrease in the late airway response compared to placebo, but it did not have any effect on the early asthmatic response.

SUMMARY OF THE INVENTION

In one embodiment, the present invention provides a method of reducing lung inflammation in a subject in need thereof, characterized by increased levels of activated white blood cells, the method comprising administering to the subject an amount of a pharmaceutical composition effective to reduce said lung inflammation, wherein the pharmaceutical composition comprises a leukotoxin (LtxA) and a pharmaceutically acceptable carrier. The activated white blood cells express a greater level of LFA-1 compared to white blood cells from a normal healthy subject, and may be further characterized as $CD11a^{hi}$ cells. The leukotoxin may be prepared from *Aggregatibacter actinomycetemcomitans*, and recombinantly. In a preferred embodiment, the leukotoxin has at least 90% homology with the peptide according to SEQ ID NO: 1. The leukotoxin may be administered orally, parenterally, intravenously, intraperitoneally or by inhalation.

In certain embodiments, the inflammation is caused by a disease or chronic disorder. The disease or chronic disorder may be asthma, cystic fibrosis, chronic obstructive pulmonary disease, an allergen, or an infection. The subject may also have a bacterial, fungal, or viral infection that causes the inflammation. The amount administered to the subject is effective to reduce local cytokine levels in bronchoalveolar lavage fluid or lung tissue, and the cytokines may be IL-4, IL-5, IL-9, IL-17F and IL-23α. In a preferred embodiment, the amount of leukotoxin administered is effective to reduce the level of at least one cytokine at least about five-fold. In a further embodiment, the pharmaceutical composition comprising leukotoxin is formulated for and administered by using an inhaler selected from the group consisting of a nebulizer, a metered-dose inhaler, and a dry powder inhaler.

In another embodiment, the present invention provides a method of treating a disease characterized by lung inflammation, the method comprising administering a pharmaceutical composition to a subject in need of such treatment in an amount effective to reduce said inflammation, wherein the pharmaceutical composition comprises a leukotoxin and a pharmaceutically acceptable carrier, and wherein the disease is selected from the group consisting of asthma, cystic fibrosis, chronic obstructive pulmonary disease, allergies, and an infection.

In another embodiment, the present invention provides a pharmaceutical composition comprising leukotoxin and a pharmaceutically acceptable carrier, wherein the pharmaceutical composition is in a form suitable for inhalation. In a further embodiment, the pharmaceutically acceptable carrier is a form of an aerosol or a dry powder.

DETAILED DESCRIPTION OF THE INVENTION

Figure 1A:
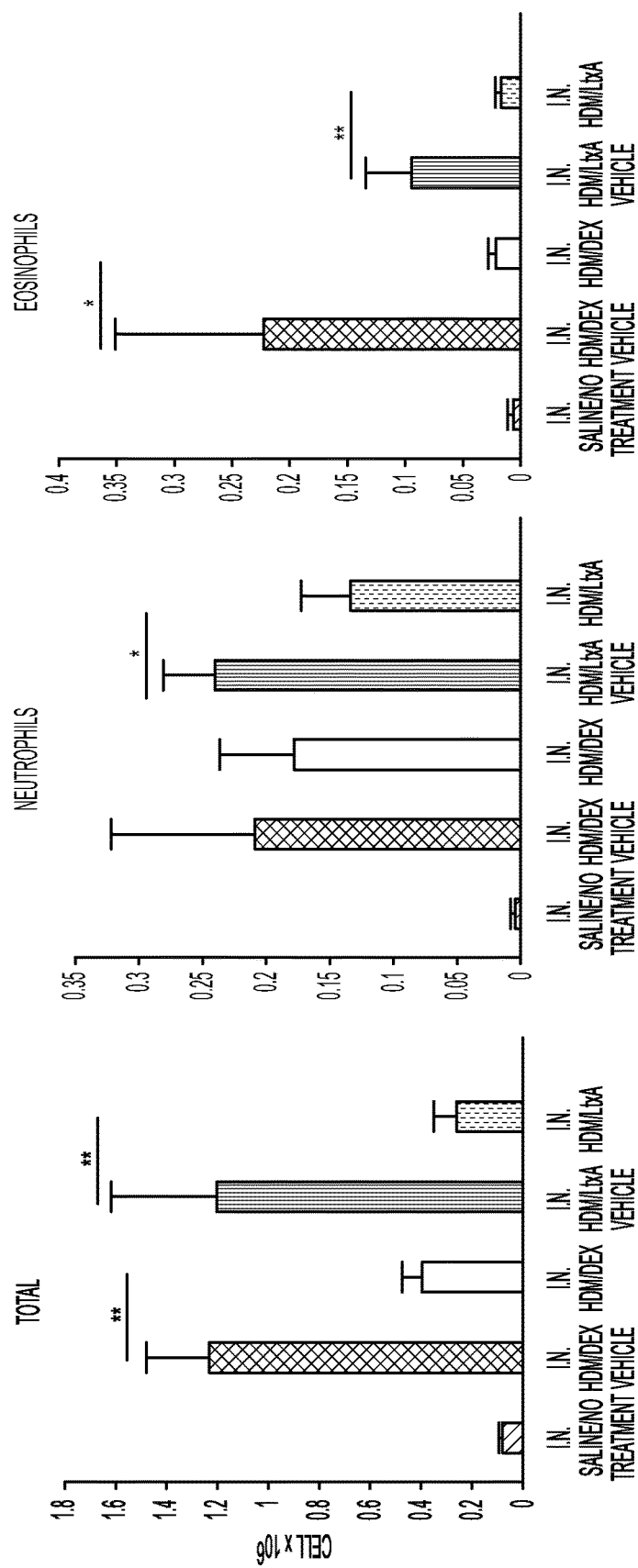
FIG. 1A-B is a set of diagrams showing the examination of white blood cells in bronchoalveolar lavage fluid (BAL) following treatment of house dust mite (HDM) exposed mice with either a vehicle (saline, HDM/Dex vehicle; or HDM/LtxA vehicle), dexamethasone (HDM/Dex) or leukotoxin (HDM/LtxA).

This invention relates to methods for treating lung inflammation using LtxA, and incorporates the discovery that administering LtxA to a patient suffering lung inflammation characterized by activated inflammatory cells expressing LFA-1 results in the rapid depletion of the activated inflammatory cells. LFA-1 is a β2-integrin expressed on the surface of white blood cells that is composed of CD11a and CD 18, and in its active conformation is involved in immune cell migration and signaling. It has now been discovered that LtxA rapidly targets all inflammatory WBCs that express the activated conformation of LFA-1 on their surface that migrate to the lung, providing a robust targeted anti-inflammatory local effect in the lung, while having little or no toxic effect on bronchial/tracheal epithelial cells.

LtxA

LtxA is a ~115 kDa protein produced by the Gram negative bacterium *Aggregatibacter actinomycetemcomitans*. LtxA binds specifically to LFA-1 and cells that lack LFA-1 are resistant to its toxicity. For example, LtxA is not active against human red blood cells, human epithelial cells, rat cells, or mouse cells. LtxA also remains active in the presence of human peripheral blood.

While many LtxA preparations can be used, highly purified LtxA is preferred. Examples include LtxA polypeptide purified from *Aggregatibacter actinomycetemcomitans* (SEQ ID NO: 1) and other variants having substantially the same biological activity as that having the sequence of SEQ ID NO: 1. It was discovered that *Aggregatibacter actinomycetemcomitans* secreted active LtxA into culture supernatants and an efficient method for its purification was described in Kachlany, S. C., et al. 2002. Protein Expr Purif 25:465-71. This method can therefore be used to prepare isolated or purified LtxA polypeptide. In one example, a purification procedure of the toxin involves:

a. inoculating a single colony of *Aggregatibacter actinomycetemcomitans* into a fresh broth and growing cultures;
 b. adding the growing cultures to fresh broth, adding glass beads and incubating;
 c. centrifuging the incubated culture, forming a pellet and a supernatant;
 d. filtering the supernatant through a membrane to provide a filtered supernatant;
 e. mixing (NH4)2SO4 and the filtered supernatant together to form a mixture;
 f. centrifuging the mixture to form a mixture pellet;
 g. resuspending the mixture pellet in buffer to form a protein resuspension;
 h. passing the protein resuspension through a column; and
 i. collecting the protein eluting off the column.

See also PCT/US2006/45258 (WO 2007/062150); US Application 20090075883 (U.S. Ser. No. 12/154,843) and PCT/US10/52453 (WO 2011/047011). The contents of these documents are incorporated herein by reference.

An "isolated polypeptide" refers to a polypeptide that has been separated from other proteins, lipids, and nucleic acids with which it is naturally associated. The polypeptide constitutes at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A functional equivalent of LtxA refers to a polypeptide derivative of the LtxA polypeptide, e.g., a protein having one or more point mutations, insertions, deletions, truncations, a fusion protein, or a combination thereof. It retains substantially the activity of the LtxA polypeptide, i.e., the ability to target and kill WBCs that express the activated conformation of LFA-1 on their surface while having little or no toxic effect on other cells or organs in the body. The isolated polypeptide can contain SEQ ID NO: 1 or a functional fragment of SEQ ID NO: 1. In general, the functional equivalent is at least 75% (e.g., any number between 75% and 100%, inclusive, e.g., 70%, 80%, 85%, 90%, 95%, and 99%) identical to SEQ ID NO: 1.

All of naturally occurring LtxA, genetic engineered LtxA, and chemically synthesized LtxA can be used to practice the invention disclosed herein. LtxA obtained by recombinant DNA technology may have the same amino acid sequence as naturally a occurring LtxA (SEQ ID NO: 1) or an functionally equivalent thereof. The term "LtxA" also covers chemically modified LtxA. Examples of chemically modified LtxA include LtxA subjected to conformational change, addition or deletion of a sugar chain, and LtxA to which a compound such as polyethylene glycol has been bound. Once purified and tested by standard methods or according to the method described in the examples below, LtxA can be included in a pharmaceutical composition, e.g., a topical composition.

The amino acid composition of the LtxA polypeptide described herein may vary without disrupting the ability of the polypeptide to target and kill WBCs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the ability to reduce inflammation and/or to identify mutants that retain the activity as described below in the examples.

"Substantially identical" as used herein refers to that the nucleic or amino acid sequence is at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence. Preferably, such variant nucleic acid and polypeptide sequences will share 75% or more (i.e. 80, 85, 90, 95, 97, 98, 99% or more) sequence identity with the sequences recited in the application. Preferably such sequence identity is calculated with regard to the full length of the reference sequence (i.e. the sequence recited in the application). In a preferred embodiment, the leukotoxin has at least 90% or greater percent homology with the peptide according to SEQ ID NO: 1.

A LtxA polypeptide as described in this invention can be obtained as a naturally occurring polypeptide or a recombinant polypeptide. To prepare a recombinant polypeptide, a nucleic acid encoding it (e.g., SEQ ID NO: 2) can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Pharmaceutical Compositions

The present invention also provides a pharmaceutical composition that contains LtxA and a pharmaceutically acceptable carrier suitable for administration to the lung. Examples of pharmaceutically acceptable carriers include, but are not limited to microparticles, dry dispersible powders, anhydrous ethanol, particles formed by spray drying, and the like, and other preparations as known in the art to be suitable for pulmonary administration. As such the pharmaceutical compositions of the present invention containing LtxA may be administered using commonly known devices configured for the delivery of pharmaceutical compositions in the form of powder or liquid aerosol particles to the bronchioles of the lung. Such devices include, but are not limited to inhalers, nebulizers, nasal sprayers, dry powder inhalation systems; ultrasonic inhalation systems; metered dose inhalers; or solution metering devices. The pharmaceutically acceptable carriers of the pharmaceutical composition of the invention may comprise a wide variety of non-active ingredients which are useful for formulation purposes and which do not materially affect the novel and useful properties of LtxA.

The term "pharmaceutically acceptable" refers to a component that is not biologically or otherwise undesirable, i.e., the component may be incorporated into a pharmaceutical composition of the invention and administered to a patient's lung without causing any undesirable biological effects or interacting in a deleterious manner with any of the other components of the formulation composition in which it is contained. When the term "pharmaceutically acceptable" is used to refer to a component other than a pharmacologically active agent, it is implied that the component has met the required standards of toxicological and manufacturing testing or that it is included on the Inactive Ingredient Guide prepared by the U.S. Food and Drug Administration.

Inhalation products are typically packaged in multidose form, for nebulizers and other inhalations systems as known in the art. Preservatives may be used to prevent microbial contamination during use. Suitable preservatives include: biguanides, hydrogen peroxide, hydrogen peroxide producers, benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1% (w/w). Unit dose formulations of the present invention will be sterile, but typically unpreserved. Such formulations, therefore, generally will not contain preservatives.

The pharmaceutical composition may further comprise antibiotics, antiviral agents, corticosteroids, β-agonists (long or short acting), leukotriene modifiers, antihistamines, phosphodiesterase inhibitors, sodium cromoglycate, Nedocromil, cytokines, and theophylline.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, cefuroxide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, derivatives thereof, and the like and mixtures thereof.

Examples of corticosteroids include cortisone, prednisolone, triamcinolone, flurometholone, dexamethasone, medrysone, loteprednol, fluazacort, hydrocortisone, prednisone triamcinolone, betamethasone, prednisone, methylprednisolone, triamcinolone acetonide, triamcinolone hexacatonide, paramethasone acetate, diflorasone, fluocinolone and fluocinonide, derivatives thereof, and mixtures thereof. Examples of antiviral agents include interferon gamma, zidovudine, amantadine hydrochloride, ribavirin, acyclovir, valciclovir, dideoxycytidine, and derivatives thereof. Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Treatment Methods

The invention provides a method of reducing lung inflammation in a subject in need thereof, characterized by increased levels of activated WBCs, by administering to the subject a pharmaceutical composition comprising leukotoxin and a pharmaceutically acceptable carrier in an amount effective to reduce lung inflammation. In another embodiment, the invention provides a method of treating a disease characterized by lung inflammation, comprising administering to a subject in need thereof a pharmaceutical composition comprising leukotoxin and a pharmaceutically acceptable carrier in an amount effective to reduce lung inflammation characterizing the disease.

In another embodiment, the invention provides a method for screening a subject for lung inflammation by requesting a biological sample from the subject, requesting an analysis of the biological sample to determine whether the subject expresses one or more biomarkers associate with lung inflammation, and then treating the subject with a pharmaceutical composition comprising LtxA. In certain embodiments, the subject is currently undergoing treatment with LtxA, and the dose of LtxA is further determined according to the presence of lung inflammation biomarkers.

Lung inflammation can be characterized by an increase in active WBCs expressing a greater level of the activated conformation of LFA-1 compared to WBC's of a healthy subject without lung inflammation. These WBCs that have a greater level of the activated conformation of LFA-1 are also referred to as $CD11a^{hi}$ cells. $CD11a^{hi}$ cells can be identified in biological samples from a subject such as lung tissue, peripheral blood mononuclear cells (PBMCs) or a BAL sample, thus a clinician can determine whether a subject is in need of treatment for lung inflammation. In another embodiment, a biological sample from a subject can also be screened for the increased expression of certain cytokines (biomarkers) to determine whether the subject is in need of a treatment for lung inflammation. These cytokines/biomarkers include IL-4, IL-5, IL-9, IL-17F and IL-23α. Standard assays are known in the art to detect cytokines in biological samples, examples of biological samples include without limitation lung tissue, peripheral blood mononuclear cells (PBMCs) or a BAL sample.

Lung inflammation can be caused by many diseases and chronic conditions, such as asthma, chronic obstructive pulmonary disease (COPD), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, bacterial infections, respiratory syncytial virus (RSV) infection, parainfluenza virus (PIV) infection, rhinovirus (RV) infection and adenovirus infection. Many of the above described diseases and chronic disorders, cause an increase of WBCs expressing the activated conformation of LFA-1 to migrate and congregate in lung tissue and BAL and are suitable for treatment by the methods of the present invention.

Cystic fibrosis (CF) is a disease characterized by chronic inflammation and immune-mediated damage to the lung and airway, resulting in respiratory failure and death. Activated LFA-1 neutrophils responding to bacterial infection are predominantly responsible for the immune-mediated injury. Neutrophils generally play a role in the elimination of bacterial pathogens, however, in the case of CF, activated LFA-1 neutrophils are less immunologically effective, thus a target for LtxA therapy. Asthma is a chronic condition that is also characterized by lung inflammation, whereby activated WBCs infiltrate into the airways and release inflammatory mediators which further cause bronchial epithelium damage. Allergic asthma is IgE mediated and involves initial exposure to an inhaled allergen and subsequent antigen presentation to T-helper type 2 lymphocytes, which secrete IL-4 and IL-13. Allergic asthma can be further characterized by airway inflammation in BAL and lung tissue, persistent Th2 response with increased cytokine production, progressive airway remodeling and bronchial hyperactivity. The WBCs to be targeted can also be characterized as $CD11a^{hi}$ cells, which are monocytes and non-helper T-cells that express LFA-1 with a Mean Fluorescent Intensity (MFI) of about $10^3$-$10^5$. In a preferred embodiment, the treatment methods of the present invention treat patients suffering asthma attacks characterized by $CD11^{hi}$ cells with an LFA-1 MFI of about $10^4$-$10^5$. One with ordinary skill in the art can identify $CD11a^{hi}$ cells by MFI using standard techniques and reagents known in the art.

COPD, or chronic obstructive pulmonary disease, is a progressive disease that makes it hard to breathe. COPD can cause coughing that produces large amounts of mucus (a slimy substance), wheezing, shortness of breath, chest tightness, and other symptoms. In COPD, less air flows in and out of the airways because of one or more of the following: the airways and air sacs lose their elastic quality; the walls between many of the air sacs are destroyed; the walls of the airways become thick and inflamed, and the airways make more mucus than usual, which can clog them.

In chronic bronchitis, the lining of the airways is constantly irritated and inflamed. This causes the lining to thicken. Lots of thick mucus forms in the airways, making it hard to breathe.

"Treating" or "treatment" refers to administration of a compound or pharmaceutical composition to a subject, who has lung inflammation, with the purpose to cure, alleviate, relieve, remedy, delay the onset of, or ameliorate lung inflammation, the symptoms of lung inflammation, the disease state secondary to lung inflammation, or the predisposition toward lung inflammation.

As used herein, the term "subject" refers to any animal (e.g., a mammal), including, but not limited to humans, non-human primates, rodents, dogs, cats, horses, cows, sheep, domesticated animals and the like, which is to be the recipient of a particular treatment. Typically, the terms "subject" and "patient" are used interchangeably herein in reference to a human subject.

A "therapeutically effective amount" refers to the amount of an agent or pharmaceutical composition sufficient to produce beneficial or desired results. A therapeutically effective amount can be administered in one or more administrations, applications or dosages and is not intended to be limited to a particular formulation or administration route.

The agent or pharmaceutical composition can be administered in vivo alone or co-administered in conjunction with other drugs or therapy. As used herein, the term "co-administration" or "co-administered" refers to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents/therapies used may vary.

It will be appreciated by persons skilled in the art that the pharmaceutical compositions of the invention may be administered locally or systemically. Routes of administration include nasal, pulmonary, buccal, parenteral (intravenous, subcutaneous, and intramuscular), and oral. Also administration from implants is possible. Suitable preparation forms are, for example granules, powders, tablets, coated tablets, (micro) capsules, microparticles, syrups, emulsions, microemulsions, defined as optically isotropic thermodynamically stable systems consisting of water, oil and surfactant, liquid crystalline phases, defined as systems characterized by long-range order but short-range disorder (examples include lamellar, hexagonal and cubic phases, either water- or oil continuous), or their dispersed counterparts, gels, dispersions, suspensions, creams, aerosols, droplets or injectable solution in ampule form and also preparations with protracted release of active compounds, in whose preparation excipients, diluents, adjuvants or carriers are customarily used as described above.

The dosage required depends on the choice of the route of administration; the nature of the formulation; the nature of the patient's illness; the subject's size, weight, surface area, age, and sex; other drugs being administered; and the judgment of the clinician. Suitable dosages are in the range of 0.01-100 mg/kg. Variations in the needed dosage are to be expected in view of the variety of compounds available that may be combined with LtxA and the different efficiencies of various routes of administration. Variations in these dosage levels can be adjusted using standard empirical routines for optimization as is well understood in the art that may be employed by the ordinarily skilled artisan without undue experimentation. Encapsulation of the compound in a suitable delivery vehicle (e.g., polymeric microparticles or implantable devices) may increase the efficiency of delivery.

In alternative preferred embodiments, the pharmaceutical composition is suitable for pulmonary administration or nasal administration.

The pharmaceutical compositions of the invention can be administered intranasally or by inhalation and are conveniently delivered in the form of a dry powder inhaler or an aerosol spray presentation of liquid or powder particles from a pressurized container, pump, spray or nebulizer with the use of a suitable propellant, e.g. dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a polypeptide of the invention and a suitable powder base such as lactose or starch.

Aerosol or dry powder formulations are preferably arranged so that each metered dose or 'puff' contains at least 0.1 mg of the LtxA polypeptide of the invention for delivery to the patient. It will be appreciated that the overall daily dose with an aerosol will vary from patient to patient, and may be administered in a single dose or, more usually, in divided doses throughout the day.

In certain embodiments, the invention provides a kit for the treatment of lung inflammation. The kit may contain multiple doses, capsules, or cartridges of a pharmaceutical composition comprising LtxA to be used in conjunction with an inhalation device to administer the LtxA pharmaceutical composition. The kit may further comprise a set of instructions to perform the methods of treatment as previously described. The kit may further comprise reagents to detect lung inflammation, or determine the efficacy of the LtxA treatment.

The following non-limiting example serves to further illustrate the invention.

EXAMPLES

Materials and Methods

LtxA Purification. LtxA was purified from culture supernatants of *A. actinomycetemcomitans* strain 4500 (Diaz et al., (2006) Microb Pathog 40, 48-55.)

Isolation of PBMCs from blood. Whole blood was collected from 8 allergic asthma patients and 11 non-allergic healthy controls who did not exhibit any allergies. All of the allergic asthma patients are ages 5-50. Patients had recent evidence of reversible airway disease on spirometry and allergy to dust mite as determined by skin testing. Patients were allowed to be on any combination of short-acting bronchodilators, inhaled corticosteroids, and long-acting bronchodilators. Patients were excluded if they were pregnant, taking omalizumab (Xolair®) or other immunotherapy treatment, systemic corticosteroids, antibiotics within 30 days, or had significant comorbidities such as HIV, heart disease, diabetes, and cancer. The control group had no history of asthma or allergic conditions. The collection protocol was approved by the Rutgers Institutional Review Board and written informed consent was obtained from all study subjects. PBMCs were isolated using ficoll density gradient separation (Corning Cellgro, Manassas, Va.). Viable cells were counted using Vi-Cell viability instrument.

Analysis of PBMCs. PBMCs ($10^6$ cells/ml) from patients and controls were stained with antibodies (Biolegend, San Diego, Calif.) to the following markers: CD4 (T helper cells), CD11a, CD14 (monocytes), and CD3 (T-cells). PBMCs from asthma patients were also incubated overnight with either buffer or LtxA (500 ng/ml) in RPMI 1640 medium. The treated PBMCs were washed with PBS and stained with annexin V along with the above antibodies and analyzed through flow cytometery to measure LtxA-mediated cell death.

Animal study. Female BALB/c mice (6-8 weeks, 15-20 g, Jackson Laboratories, Bar Harbor, Me.) were housed under specific pathogen-free conditions and a 12-hour light/dark cycle with access to food and water. Under isoflurane anesthesia, mice were exposed to HDM extract (*D. pteronyssinus*; Greer Laboratories, Lenoir, N.C.) intranasally (25 μg in 10 μl of saline per nostril). Control (non-asthmatic) animals were administered an equal volume of saline alone (saline/no treatment, FIGS. 1 and 2). The frequency of exposure for HDM/saline was 5 days/week, for a total of 5 weeks. Power calculations from pilot studies indicated that four animals per group were sufficient to detect a significant difference between control and experimental groups.

After two weeks, HDM-exposed mice were divided into 4 groups of 4 mice/group and treated with (1) dexamethasone vehicle, saline (HDM/Dex vehicle, FIGS. 1 and 2) subcutaneously (s.c.) once daily, five days per week, (2) dexamethasone, Sigma; 1.25 mg/kg (HDM/Dex, FIGS. 1 and 2) s.c. once daily, five days per week, (3) LtxA vehicle, buffer (HDM/LtxA vehicle, FIGS. 1 and 2) intraperitoneally (i.p.), three days per week, and (4) LtxA, 0.5 mg/kg (HDM/LtxA, FIGS. 1 and 2) i.p., three days per week. HDM exposure was continued throughout the 3-week treatment period.

BAL fluid from each mouse was subjected to RBC lysis for 10 minutes at room temperature, followed by washing twice at 400×g for 5 minutes and resuspending the cell pellet in PBS. Total BAL fluid cell number was counted using a hemocytometer. Immunophenotypic analysis of BAL fluid cells was performed by antibody staining and flow cytometry. For each antibody stain, $10^6$ cells were first blocked with Fc blocker (rat anti-mouse CD16/CD32, BD Biosciences, San Jose, Calif.) for 10 minutes at room temperature, followed by incubation with monoclonal antibodies at 4° C. for 30 minutes and analysis on an LSR II flow cytometer (BD Biosciences). Antibodies (BD Biosciences) to the following markers were used to identify the various cellular subtypes: CD3e (T-cells), CD45R/B220 (B-cells), Ly6G, CCR3 (neutrophils), CCR3, Ly6G (eosinophils), MHC II (macrophages). Relevant isotype controls were included with each experiment.

Blood from the mice was collected by ileac vein puncture immediately following the BAL fluid isolation. Blood was collected in anticoagulant tubes and centrifuged at 400×g for 10 minutes.

Lung tissue histology. After collecting BAL fluid and blood, lungs were removed through dissection and stored in 10% neutral buffered formalin at room temperature until microscopic analysis. Sections of paraffin embedded fixed lung tissues were stained with H&E to analyze total lung inflammation. Sections were also stained with periodic acid Schiff reagent to identify mucous and goblet cell hyperplasia and Sirius red for eosinophils. The tissue preparation and examination was carried out at the New Jersey Medical School Histology Core Facility. Samples were examined by a board certified pathologist.

Cytokine Analysis. Quantitative RT-PCR was used to determine the expression levels of proinflammatory cytokines (IL-4, 5, 9, 17F and 23a) in the lungs of mice. Total RNA from the lung tissue was extracted with Trizol reagent (Life Technologies, Grand Island, N.Y.). Relative mRNA levels were determined by qRT-PCR. One microgram of total RNA was reverse transcribed using High Capacity cDNA Reverse Transcription Kit (Life Technologies, Grand Island, N.Y.). Amplification was carried out using TaqMan Fast Universal PCR Master Mix (Life Technologies, Grand Island, N.Y.). The data was normalized to glyceraldehyde 3-phosphate dehydrogenase (GAPDH). Gene expression was calculated using the $\Delta\Delta CT$ method relative to naïve sample.

Statistical analysis. BAL fluid cell counts, differential cell counts, and cytokine levels were compared by Students t-test. A p value of $\leq 0.05$ was considered significant.

Results

Expression of LFA-1 on WBCs from allergic asthma patients and healthy controls. We analyzed peripheral blood mononuclear cells (PBMCs) from the blood of eight allergic asthma patients and eleven matched healthy controls. Patients diagnosed with asthma tested positive for an allergic reaction to house dust mite. From the total PBMC population, the percentage of CD11a (LFA-1) positive cells from patients was significantly higher than from the healthy controls. Patients had 95.1±3.14% CD11a positive cells while healthy controls had 90.3±4.11%. In addition, the number of LFA-1 molecules on the surface of CD11a$^+$ WBCs from allergic asthma patients (8605±2519) was significantly greater than on the surface of healthy control WBCs (5089±2107) as indicated by the mean fluorescence intensity (MFI).

WBCs stained with anti-CD4 and anti-CD 11a antibodies revealed a unique cellular population in allergic asthma patients that consisted of CD4$^-$CD11a$^{hi}$ cells (MFI $10^4$-$10^5$), which was absent from the healthy control samples. Immunophenotypic analysis revealed that this CD11a$^{hi}$ population in asthma samples consisted primarily of CD14$^+$ monocytes and CD3$^+$ non-helper T-cells. Thus, high LFA-1 expression defines a unique cellular population that is present in patients with allergic asthma.

Effects of LtxA on PBMCs from allergic asthma patients. To determine which cells from patients are targeted by LtxA, PBMC samples were treated with LtxA for 24 hours and then stained with annexin V and analyzed by flow cytometry. Of the CD11a$^+$PBMCs, LtxA killed only the CD11a$^{hi}$ cells and did not affect cells that had low expression of LFA-1. Cells were killed by both apoptosis (annexin V positive) and depletion. The cells that were depleted by LtxA express active state LFA-1 as revealed by staining with an antibody (mAb24) that recognizes specifically LFA-1 in the active conformation. The majority of these cells also stained positive for CD14, indicating that they were monocytes.

Evaluation of LtxA in a mouse model for allergic asthma. Given the potential role that LFA-1 plays in the pathogenesis of allergic asthma and the ability for LtxA to target specifically the LFA-1$^{hi}$ WBCs ex vivo that are unique to allergic asthma patients, an initial proof-of-principle evaluation of LtxA in a mouse model for allergic asthma was performed.

Mice were administered house dust mite (HDM) extract or saline intranasally (i.n.) five days per week for five weeks. After two weeks of administration, HDM-exposed mice were subdivided into four groups of four mice per group and received the following treatments for an additional three weeks: dexamethasone vehicle, subcutaneous (s.c.) 5 days/week; dexamethasone (1.25 mg/kg), s.c. 5 days/week; LtxA vehicle, intraperitoneal (i.p.) 3 days/week; LtxA (0.5 mg/kg), i.p. 3 days/week.

Figure 1B:
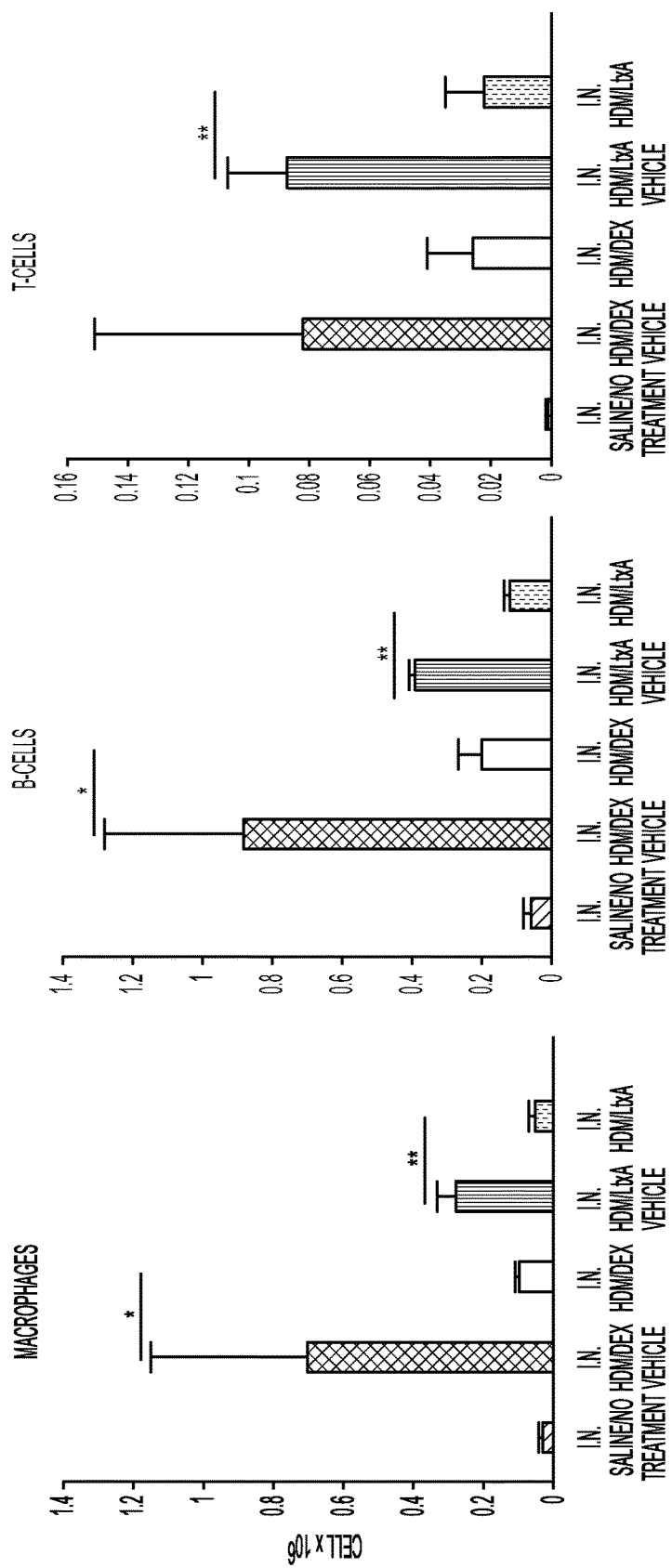

At the end of the study, bronchoalveolar lavage (BAL) fluid, lung tissue, and blood were collected from all mice for further evaluation. Examination of WBCs in the BAL fluid revealed that HDM-exposed mice treated with the dexamethasone vehicle or LtxA vehicle had significantly higher levels of all WBC subsets than mice that were given only saline (FIGS. 1A and 1B). Treatment of HDM-exposed mice with dexamethasone or LtxA caused significant reduction in the numbers of WBCs in the BAL fluid.

To determine if LFA-1 is involved in the migration of WBCs to the lung tissue in this animal model, the levels of LFA-1 on PBMCs and BAL fluid WBCs in two HDM-exposed mice that were treated with LtxA vehicle were examined. The migrated WBCs that were present in the BAL fluid had significantly higher levels of LFA-1 than on the WBCs in the peripheral blood of the same animal.

Lung tissue was sectioned and stained with H&E, PAS, or Sirius Red. H&E staining revealed a large infiltration of WBCs in the lung tissue of HDM-exposed mice treated with dexamethasone vehicle or LtxA vehicle. Infiltration was not evident in saline-exposed mice. The infiltration of WBCs in HDM-exposed mice was most evident surrounding the blood vessels and bronchioles. Significant goblet cell hyperplasia surrounding many of the bronchioles in the vehicle-treated controls, but not in the other samples was observed. Staining of polysaccharides with PAS in the lung tissue from LtxA vehicle-treated mice confirmed the presence of mucin-producing goblet cells and subepithelial accumulation of collagen. Sirius Red staining of sections revealed pink-staining eosinophils in the vehicle-treated mice, but not in the LtxA-treated mice. Mice that were treated with dexamethasone had a reduced number of eosinophils compared to the vehicle control, but still greater than LtxA-treated mice.

Figure 2:
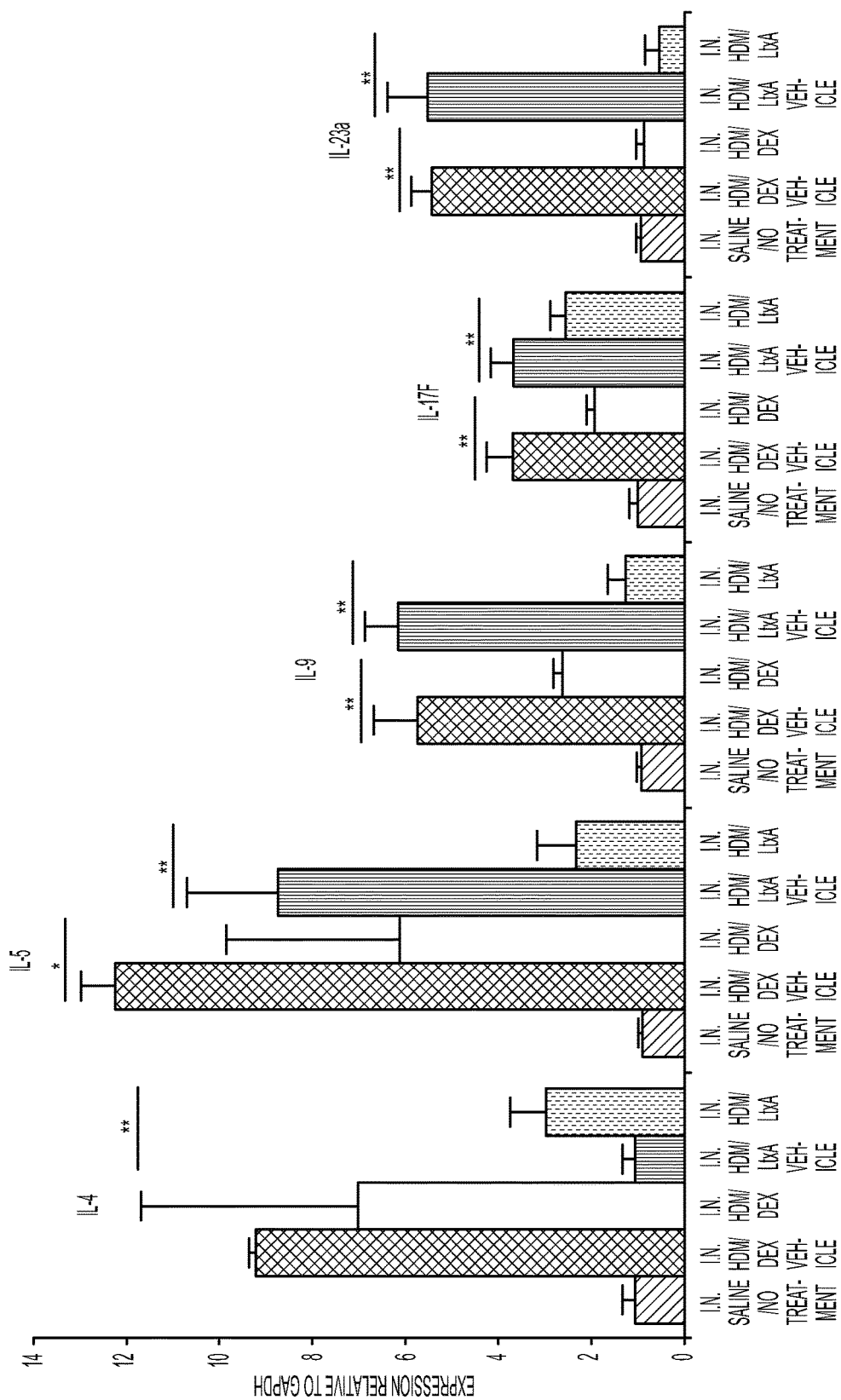
FIG. 2 is a diagram showing the examination of cytokines in lung tissue following treatment of house dust mite (HDM) exposed mice with either a vehicle (saline, HDM/Dex vehicle; or HDM/LtxA vehicle); dexamethasone (HDM/Dex); or leukotoxin (HDM/LtxA).

Proinflammatory cytokines play a crucial role in the pathogenesis of allergic asthma and other inflammatory conditions. In allergic asthma, IL-4, IL-5, IL-9, IL-17F, and IL-23α are the primary signaling molecules involved in disease. The levels of IL-4, IL-5, IL-9, IL-17F, and IL-23α mRNA in the lung tissue from all mice were evaluated (FIG. 2). The vehicle-treated mice had significantly greater expression of the proinflammatory cytokines compared to saline-exposed mice. In addition, dexamethasone caused reduction of IL-9, IL-17F, and IL-23α while LtxA treatment caused significant reduction of all the cytokines that were examined.

All publications cited in the specification, both patent publications and non-patent publications, are indicative of the level of skill of those reasonably skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of reducing lung inflammation in a subject in need thereof, characterized by increased levels of activated white blood cells, the method comprising administering to the subject an amount of a pharmaceutical composition effective to reduce said lung inflammation, wherein the pharmaceutical composition comprises a leukotoxin and a pharmaceutically acceptable carrier, and wherein the amount of the pharmaceutical composition administered to said subject is effective to reduce local cytokine levels in bronchoalveolar lavage fluid or lung tissue.

2. The method of claim 1, wherein the activated white blood cells are CD $11a^{hi}$ cells.

3. The method of claim 1, wherein the leukotoxin is prepared from *Aggregatibacter actinomycetemcomitans*.

4. The method of claim 1, wherein the leukotoxin consists essentially of a peptide according to SEQ ID NO: 1.

5. The method of claim 1, wherein the pharmaceutical composition is administered orally, parenterally, intravenously, intraperitoneally or by inhalation.

6. The method of claim 1, wherein the inflammation is caused by a disease or chronic disorder.

7. The method of claim 6, wherein the disease or chronic disorder is an infection, wherein the infection is a bacterial, fungal, or viral infection.

8. The method of claim 1, wherein one or more of the cytokines are selected from the group consisting of IL-4, IL-5, IL-9, IL-17F and IL-23α.

9. The method of claim 8, wherein the amount administered is effective to reduce the level of at least one of said cytokines at least five-fold.

10. The method of claim 1, wherein the pharmaceutical composition is administered by using an inhaler selected from the group consisting of a nebulizer, a metered-dose inhaler, and a dry powder inhaler.

11. A method of treating a disease characterized by lung inflammation, the method comprising administering a pharmaceutical composition to a subject in need of such treatment in an amount effective to reduce said inflammation, wherein:

the pharmaceutical composition comprises a leukotoxin and a pharmaceutically acceptable carrier, the amount administered to a subject is effective to reduce local cytokine levels in bronchoalveolar lavage fluid or lung tissue, and the disease is selected from the group consisting of asthma, cystic fibrosis, chronic obstructive pulmonary disease, allergies, and an infection.

12. The method of claim 11, wherein the leukotoxin consists essentially of a peptide according to SEQ ID NO: 1.

13. The method of claim 11, wherein the pharmaceutical composition is administered by using an inhaler selected from the group consisting of a nebulizer, a metered-dose inhaler, and a dry powder inhaler.

14. The method of claim 11, wherein one or more of the cytokines are selected from the group consisting of IL-4, IL-5, IL-9, IL-17F and IL-23α.

15. The method of claim 14, wherein the amount administered is effective to reduce the level of at least one of said cytokines at least five-fold.

* * * * *

SEQUENCE LISTING

<160> NUMBER OF SEQ ID NOS: 2

<210> SEQ ID NO 1
<211> LENGTH: 1055
<212> TYPE: PRT
<213> ORGANISM: Aggregatibacter actinomycetemcomitans

<400> SEQUENCE: 1

```
Met Ala Thr Thr Ser Leu Leu Asn Thr Lys Gln Gln Ala Ala Gln Phe
1               5                   10                  15

Ala Asn Ser Val Ala Asp Arg Ala Lys Glu Asn Ile Asp Ala Ala Lys
            20                  25                  30

Glu Gln Leu Gln Lys Ala Leu Asp Lys Leu Gly Lys Thr Gly Lys Lys
        35                  40                  45

Leu Thr Leu Tyr Ile Lys Asn Tyr Lys Lys Gly Asn Gly Leu Thr Ala
50                  55                  60

Leu Ile Lys Ala Ala Gln Lys Leu Gly Ile Glu Val Tyr His Glu Gly
65                  70                  75                  80

Lys Asp Gly Pro Ala Leu Thr Asn Gly Ile Leu Asn Thr Gly Lys Lys
                85                  90                  95

Leu Leu Gly Leu Thr Glu Arg Gly Leu Thr Leu Phe Ala Pro Glu Leu
            100                 105                 110

Asp Lys Trp Ile Gln Gly Asn Lys His Leu Ser Asn Ser Val Gly Ser
        115                 120                 125

Thr Gly Asn Leu Thr Lys Ala Ile Asp Lys Val Gln Ser Val Leu Gly
130                 135                 140

Thr Leu Gln Ala Phe Leu Asn Thr Ala Phe Ser Gly Met Asp Leu Asp
145                 150                 155                 160

Ala Leu Ile Lys Ala Arg Gln Asn Gly Lys Asn Val Thr Asp Val Gln
                165                 170                 175

Leu Ala Lys Ala Ser Leu Asn Leu Ile Asn Glu Leu Ile Gly Thr Ile
            180                 185                 190

Ser Ser Ile Thr Asn Asn Val Asp Thr Phe Ser Lys Gln Leu Asn Lys
        195                 200                 205

Leu Gly Glu Ala Leu Gly Gln Val Lys His Phe Gly Ser Phe Gly Asp
210                 215                 220

Lys Leu Lys Asn Leu Pro Lys Leu Gly Asn Leu Gly Lys Gly Leu Gly
225                 230                 235                 240

Ala Leu Ser Gly Val Leu Ser Ala Ile Ser Ala Ala Leu Leu Leu Ala
                245                 250                 255

Asn Lys Asp Ala Asp Thr Ala Thr Lys Ala Ala Ala Ala Ala Glu Leu
            260                 265                 270

Thr Asn Lys Val Leu Gly Asn Ile Gly Lys Ala Ile Thr Gln Tyr Leu
        275                 280                 285

Ile Ala Gln Arg Ala Ala Ala Gly Leu Ser Thr Thr Gly Pro Val Ala
            290                 295                 300

Gly Leu Ile Ala Ser Val Val Ser Leu Ala Ile Ser Pro Leu Ser Phe
305                 310                 315                 320

Leu Gly Ile Ala Lys Gln Phe Asp Arg Ala Arg Met Leu Glu Glu Tyr
                325                 330                 335

Ser Lys Arg Phe Lys Lys Phe Gly Tyr Asn Gly Asp Ser Leu Leu Gly
            340                 345                 350

Gln Phe Tyr Lys Asn Thr Gly Ile Ala Asp Ala Ala Ile Thr Thr Ile
        355                 360                 365
```

-continued

```
Asn Thr Val Leu Ser Ala Ile Ala Ala Gly Val Gly Ala Ser Ala
    370                 375                 380
Gly Ser Leu Val Gly Ala Pro Ile Gly Leu Leu Val Ser Ala Ile Thr
385                 390                 395                 400
Ser Leu Ile Ser Gly Ile Leu Asp Ala Ser Lys Gln Ala Val Phe Glu
                405                 410                 415
His Ile Ala Asn Gln Leu Ala Asp Lys Ile Lys Ala Trp Glu Asn Lys
            420                 425                 430
Tyr Gly Lys Asn Tyr Phe Glu Asn Gly Tyr Asp Ala Arg His Ser Ala
        435                 440                 445
Phe Leu Glu Asp Ser Leu Lys Leu Phe Asn Glu Leu Arg Glu Lys Tyr
450                 455                 460
Lys Thr Glu Asn Ile Leu Ser Ile Thr Gln Gln Gly Trp Asp Gln Arg
465                 470                 475                 480
Ile Gly Glu Leu Ala Gly Ile Thr Arg Asn Gly Asp Arg Ile Gln Ser
                485                 490                 495
Gly Lys Ala Tyr Val Asp Tyr Leu Lys Lys Gly Glu Glu Leu Ala Lys
            500                 505                 510
His Ser Asp Lys Phe Thr Lys Gln Ile Leu Asp Pro Ile Lys Gly Asn
        515                 520                 525
Ile Asp Leu Ser Gly Ile Lys Gly Ser Thr Thr Leu Thr Phe Leu Asn
530                 535                 540
Pro Leu Leu Thr Ala Gly Lys Glu Glu Arg Lys Thr Arg Gln Ser Gly
545                 550                 555                 560
Lys Tyr Glu Phe Ile Thr Glu Leu Lys Val Lys Gly Arg Thr Asp Trp
                565                 570                 575
Lys Val Lys Gly Val Pro Asn Ser Asn Gly Val Tyr Asp Phe Ser Asn
            580                 585                 590
Leu Ile Gln His Ala Val Thr Arg Asp Asn Lys Val Leu Glu Ala Arg
        595                 600                 605
Leu Ile Ala Asn Leu Gly Ala Lys Asp Asp Tyr Val Phe Val Gly Ser
610                 615                 620
Gly Ser Thr Ile Val Asn Ala Gly Asp Gly Tyr Asp Val Val Asp Tyr
625                 630                 635                 640
Ser Lys Gly Arg Thr Gly Ala Leu Thr Ile Asp Gly Arg Asn Ala Thr
                645                 650                 655
Lys Ala Gly Gln Tyr Lys Val Glu Arg Asp Leu Ser Gly Thr Gln Val
            660                 665                 670
Leu Gln Glu Thr Val Ser Lys Gln Glu Thr Lys Arg Gly Lys Val Thr
        675                 680                 685
Asp Leu Leu Glu Tyr Arg Asn Tyr Lys Leu Asp Tyr Tyr Tyr Thr Asn
690                 695                 700
Lys Gly Phe Lys Ala His Asp Glu Leu Asn Ser Val Glu Glu Ile Ile
705                 710                 715                 720
Gly Ser Thr Leu Arg Asp Lys Tyr Gly Ser Lys Phe Asn Asp Val
                725                 730                 735
Phe His Gly His Asp Gly Asp Leu Ile Tyr Gly Tyr Asp Gly Asp
            740                 745                 750
Asp Arg Leu Tyr Gly Asp Asn Gly Asn Asp Glu Ile His Gly Gly Gln
        755                 760                 765
Gly Asn Asp Lys Leu Tyr Gly Ala Gly Asn Asp Arg Leu Phe Gly
770                 775                 780
Glu Tyr Gly Asn Asn Tyr Leu Asp Gly Gly Glu Gly Asp Asp His Leu
```

```
                      785               790               795               800
Glu Gly Gly Asn Gly Ser Asp Ile Leu Arg Gly Gly Ser Gly Asn Asp
                805               810               815

Lys Leu Phe Gly Asn Gln Gly Asp Asp Leu Leu Asp Gly Gly Glu Gly
            820               825               830

Asp Asp Gln Leu Ala Gly Gly Glu Gly Asn Asp Ile Tyr Val Tyr Arg
        835               840               845

Lys Glu Tyr Gly His His Thr Ile Thr Glu His Ser Gly Asp Lys Asp
    850               855               860

Lys Leu Ser Leu Ala Asn Ile Asn Leu Lys Asp Val Ser Phe Glu Arg
865               870               875               880

Asn Gly Asn Asp Leu Leu Lys Thr Asn Asn Arg Thr Ala Val Thr
                885               890               895

Phe Lys Gly Trp Phe Ser Lys Pro Asn Ser Ser Ala Gly Leu Asp Glu
            900               905               910

Tyr Gln Arg Lys Leu Leu Glu Tyr Ala Pro Glu Lys Asp Arg Ala Arg
        915               920               925

Leu Lys Arg Gln Phe Glu Leu Gln Arg Gly Lys Val Asp Lys Ser Leu
    930               935               940

Asn Asn Lys Val Glu Glu Ile Ile Gly Lys Asp Gly Glu Arg Ile Thr
945               950               955               960

Ser Gln Asp Ile Asp Asn Leu Phe Asp Lys Ser Gly Asn Lys Lys Thr
                965               970               975

Ile Ser Pro Gln Glu Leu Ala Gly Leu Ile Lys Asn Lys Gly Lys Ser
            980               985               990

Ser Ser Leu Met Ser Ser Ser Arg Ser Ser Ser Met Leu Thr Gln Lys
        995               1000              1005

Ser Gly Leu Ser Asn Asp Ile Ser Arg Ile Ile Ser Ala Thr Ser
    1010              1015              1020

Gly Phe Gly Ser Ser Gly Lys Ala Leu Ser Ala Ser Pro Leu Gln
    1025              1030              1035

Thr Asn Asn Asn Phe Asn Ser Tyr Ala Asn Ser Leu Ala Thr Thr
    1040              1045              1050

Ala Ala
    1055

<210> SEQ ID NO 2
<211> LENGTH: 3168
<212> TYPE: DNA
<213> ORGANISM: Aggregatibacter actinomycetemcomitans

<400> SEQUENCE: 2
atggcaacta cttcactgct aaatacaaaa cagcaagctg cacagtttgc aaattcagtt     60
gcagatagag ctaaggaaaa tattgatgct gcaaagaac  aattgcaaaa ggcgttagat    120
aaattaggga gacaggtaa  gaaattaact ttatatatcc ctaagaatta caaaaaagga    180
aatggtctta ctgcgcttat aaaagcagca cagaagttag ggattgaagt atatcatgaa    240
gggaaagacg gcccggcatt aactaatggt attttaaata ctgggaaaaa attacttggt    300
cttaccgaac gaggtttaac tttatttgct ccggaattag ataaatggat tcaaggtaat    360
aaacatttaa gtaattctgt gggtagtact ggaaatttga caaaagcgat agataaggtt    420
cagagtgttc ttggtacgtt acaagcgttt ttgaacaccg cattttcggg catggattta    480
gatgccttaa ttaaagcccg tcaaaatggt aaaaatgtaa cagatgtaca gctagcaaaa    540
```

```
gccagtctta  aacctgattaa  tgaattgatt  ggtactattt  ctagcattac  aaataatgta   600 gatactttt   ctaaacaact   taataagtta  ggtgaagcac  taggacaagt  aaaacatttt   660
ggtagttttg  gagataaatt   aaagaattta  cctaagttag  gtaatcttgg  aaaaggttta   720
ggtgcattat  ccggtgtatt   gtcggctata  tcagcggctc  tattacttgc  aaataaagat   780
gctgatactg  caacgaaagc   agcggctgca  gctgaattga  caaataaagt  gctaggtaac   840
atcggtaaag  cgatcacaca   atacttgatt  gctcaacgtg  ctgcagcggg  gctttctact   900
acgggacctg  tcgcagggtt   aattgcctct  gtggtcagct  tggcaatcag  ccctttgtct   960
ttcctaggta  ttgcgaaaca   atttgatcgt  gcgagaatgc  ttgaggaata  ctcgaaacgc  1020
tttaagaaat  ttggttataa   cggcgatagt  ttacttggtc  aattctacaa  aaatacaggg  1080
atcgcagatg  ctgcgattac   aacgattaac  actgtattaa  gtgctattgc  agcagggtt   1140 ggtgcagcct  ccgccggttc   tttagttggt  gcgccaatcg  gtttgttagt  gagtgcgatt  1200
accagcttaa  tttcaggaat   tcttgatgct  tctaaacaag  ccgttttga   acatatcgcg  1260 aatcagctcg  ccgataaaat   taaagcatgg  gagaataagt  acggtaagaa  ttactttgaa  1320
aatggctatg  atgcccgtca   ttccgccttc  ttggaagatt  cactaaaatt  atttaatgag  1380
ttacgtgaaa  aatataaaac   cgaaaatata  ttatctatca  ctcaacaagg  ttgggatcag  1440
cgcattggtg  aattagcagg   tatcactcgt  aatggagatc  gtattcaaag  tggtaaagct  1500
tatgtggatt  atttgaaaaa   gggtgaggag  cttgcaaagc  atagcgataa  attcactaaa  1560
cagattttag  atccaatcaa   aggtaatatt  gatctttcgg  gtataaaagg  ttctaccact  1620 ctaactttt   taaatccgtt   gttaaccgca  ggtaaggaag  aacggaaaac  acgtcagtca  1680
ggtaaatatg  aatttattac   tgaattaaaa  gtaaaaggac  gtaccgattg  gaaggtaaaa  1740
ggtgttccta  attctaatgg   tgtatatgat  ttttctaact  taattcaaca  tgccgttaca  1800
cgtgataata  aagttctaga   agcaagatta  attgctaatt  tgggtgctaa  agatgattat  1860 gttttgtcg   gatccggttc   aacaatagtt  aatgctggag  acggttatga  tgtggtggac  1920
tatagtaaag  gtcgcaccgg   tgcattaaca  atcgacggtc  gtaatgctac  taaagccgga  1980
caatataagg  ttgaaagaga   tcttagcggt  actcaagtct  tgcaggaaac  cgtatcaaag  2040
caagaaacta  aacgagggaa   ggttaccgat  ctacttgaat  atcgtaacta  taaattagat  2100
tactattata  cgaataaggg   cttaaagct   catgatgaat  taaactcagt  agaggaaatt  2160
atcggcagca  cactacgtga   taaatttat   ggttctaaat  ttaatgatgt  tttccatggt  2220
cacgatggcg  atgatttgat   ttatggttat  gatggcgatg  atcgtttgta  tggcgataat  2280
gggaatgacg  aaattcatgg   cggccaaggt  aatgataagc  tctatggtgg  tgccggtaac  2340
gataggctct  ttggtgaata   tggcaacaac  tatcttgacg  gtggagaagg  cgacgaccac  2400
ttagagggag  gcaatggttc   cgatattcta  agaggtggaa  gtggcaatga  taagttgttt  2460
ggaaaccaag  gagatgattt   acttgacggt  ggagaaggcg  atgaccaact  tgccggtgga  2520
gaaggaaatg  atatttatgt   ttaccgtaaa  gaatatgggc  accacactat  tacgaaacat  2580
agcggtgata  aagataaatt   atcattagca  aatatcaatc  tcaaagatgt  gtcatttgag  2640
cgtaacggca  atgatctact   attgaaaaca  aataatagaa  cagcagtaac  atttaaagga  2700
tggtttagta  aacctaattc   atcggcagga  ttagatgagt  atcaaagaaa  acttcttgaa  2760
tacgcacctg  aaaaggatcg   tgcacgactt  aagagacaat  ttgagttaca  gcgaggtaaa  2820
gtcgacaaat  cactcaataa   taagttgaa   gaaattatcg  gtaaagatgg  ggagcggatt  2880
acttcgcaag  acattgataa   tctttttgat  aagagtggga  acaaaaagac  aatttcacct  2940
```

-continued

```
caagagcttg ccggacttat taagaataaa ggtaagtcaa gtagccttat gtcttcttct   3000
cgttcgtcaa gtatgcttac acaaaagtcc ggtttgtcaa atgatattag tcgtattatt   3060
tcagcaacca gtggttttgg ttcatccggt aaagcgttat ccgcttcgcc attgcagacc   3120
aataataact ttaactctta cgcaaattcg ttagcaacta ctgcggcc                 3168
```